(12) United States Patent
Eggen et al.

(10) Patent No.: US 11,684,775 B2
(45) Date of Patent: *Jun. 27, 2023

(54) INTERVENTIONAL MEDICAL DEVICE AND METHOD OF USE

(71) Applicant: Medtronic, Inc., Minneapolis, MN (US)

(72) Inventors: Michael D. Eggen, Chisago City, MN (US); James K. Carney, Roseville, MN (US); Matthew D. Bonner, Plymouth, MN (US); Vladimir Grubac, Brooklyn Park, MN (US); Douglas S. Hine, Forest Lake, MN (US); Thomas D. Brostrom, Wayzata, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 671 days.

This patent is subject to a terminal disclaimer.

(21) Appl. No.: 16/686,617

(22) Filed: Nov. 18, 2019

(65) Prior Publication Data

US 2020/0078585 A1 Mar. 12, 2020

Related U.S. Application Data

(63) Continuation of application No. 14/518,261, filed on Oct. 20, 2014, now Pat. No. 10,478,620.

(Continued)

(51) Int. Cl.
*A61N 1/05* (2006.01)
*A61N 1/375* (2006.01)

(52) U.S. Cl.
CPC .......... *A61N 1/057* (2013.01); *A61N 1/3756* (2013.01); *A61N 1/37518* (2017.08)

(58) Field of Classification Search
CPC ... A61N 1/057; A61N 1/37518; A61N 1/3756
See application file for complete search history.

(56) References Cited

U.S. PATENT DOCUMENTS

| 3,814,104 A | 6/1974 | Irnich et al. |
| 3,835,864 A * | 9/1974 | Rasor ............... A61N 1/37518 |
| | | 607/35 |

(Continued)

FOREIGN PATENT DOCUMENTS

| EP | 1365702 A1 | 12/2003 |
| EP | 1670360 A2 | 6/2006 |

(Continued)

OTHER PUBLICATIONS

Haqqani et al., "The Implantable Cardioverter-Defibrillator Lead: Principles, Progress and Promises," PACE, vol. 32, Oct. 2009, pp. 1336-1353.

(Continued)

*Primary Examiner* — Richard G Louis
(74) *Attorney, Agent, or Firm* — Shumaker & Sieffert, P.A.

(57) ABSTRACT

A relatively compact implantable medical device includes a fixation member formed by a plurality of fingers mounted around a perimeter of a distal end of a housing of the device; each finger is elastically deformable from a relaxed condition to an extended condition, to accommodate delivery of the device to a target implant site, and from the relaxed condition to a compressed condition, to accommodate wedging of the fingers between opposing tissue surfaces at the target implant site, wherein the compressed fingers hold a cardiac pacing electrode of the device in intimate tissue contact for the delivery of pacing stimulation to the site. Each fixation finger is preferably configured to prevent penetration thereof within the tissue when the fingers are compressed and wedged between the opposing tissue sur- (Continued)

faces. The pacing electrode may be mounted on a pacing extension, which extends distally from the distal end of the device housing.

20 Claims, 9 Drawing Sheets

Related U.S. Application Data (60) Provisional application No. 62/041,954, filed on Aug. 26, 2014.

(56) References Cited

U.S. PATENT DOCUMENTS

| | | | |
|---|---|---|---|
| 3,902,501 A | 9/1975 | Citron et al. | |
| 3,939,843 A * | 2/1976 | Smyth | A61N 1/057 607/126 |
| 3,943,936 A | 3/1976 | Rasor et al. | |
| 4,103,690 A | 8/1978 | Harris | |
| 4,142,530 A | 3/1979 | Wittkampf | |
| 4,269,198 A | 5/1981 | Stokes | |
| 4,280,512 A | 7/1981 | Karr | |
| 4,424,551 A | 1/1984 | Stevenson et al. | |
| 4,858,623 A | 8/1989 | Bradshaw et al. | |
| 4,936,823 A | 6/1990 | Colvin | |
| 5,184,625 A | 2/1993 | Cottone, Jr. et al. | |
| 5,193,540 A | 3/1993 | Schulman et al. | |
| 5,411,535 A | 5/1995 | Fujii et al. | |
| 5,492,119 A | 2/1996 | Abrams | |
| 5,573,540 A | 11/1996 | Yoon | |
| 5,642,736 A | 7/1997 | Avitall | |
| 5,683,447 A | 11/1997 | Bush et al. | |
| 5,836,960 A | 11/1998 | Kolesa et al. | |
| 5,916,214 A | 6/1999 | Cosio et al. | |
| 6,007,558 A | 12/1999 | Ravenscroft et al. | |
| 6,151,525 A | 11/2000 | Soykan et al. | |
| 6,152,144 A | 11/2000 | Lesh et al. | |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,575,967 B1 | 6/2003 | Leveen et al. | |
| 6,582,443 B2 | 6/2003 | Cabak et al. | |
| 6,716,238 B2 | 4/2004 | Elliott | |
| 6,783,499 B2 | 8/2004 | Schwartz | |
| 6,915,149 B2 | 7/2005 | Ben-Haim | |
| 6,941,169 B2 | 9/2005 | Pappu | |
| 6,978,178 B2 | 12/2005 | Sommer et al. | |
| 7,149,587 B2 | 12/2006 | Wardle et al. | |
| 7,290,743 B2 | 11/2007 | Nowack | |
| 7,418,298 B2 | 8/2008 | Shiroff et al. | |
| 7,497,844 B2 | 3/2009 | Spear et al. | |
| 7,509,169 B2 | 3/2009 | Eigler et al. | |
| 7,515,971 B1 * | 4/2009 | Doan | A61B 5/0215 600/375 |
| 7,566,336 B2 | 7/2009 | Corcoran et al. | |
| 7,623,899 B2 | 11/2009 | Worley et al. | |
| 7,647,124 B2 | 1/2010 | Williams | |
| 8,032,220 B2 | 10/2011 | Kuzma | |
| 8,353,940 B2 | 1/2013 | Benderev | |
| 8,473,023 B2 | 6/2013 | Worley et al. | |
| 8,500,733 B2 | 8/2013 | Watson | |
| 8,634,919 B1 | 1/2014 | Hou et al. | |
| 8,795,328 B2 | 8/2014 | Miles et al. | |
| 9,119,959 B2 | 9/2015 | Rys et al. | |
| 9,155,882 B2 | 10/2015 | Grubac et al. | |
| 9,283,381 B2 | 3/2016 | Grubac et al. | |
| 9,526,522 B2 | 12/2016 | Wood et al. | |
| 9,675,798 B2 | 6/2017 | Grubac et al. | |
| 10,071,243 B2 | 9/2018 | Kuhn et al. | |
| 10,478,620 B2 | 11/2019 | Eggen et al. | |
| 2002/0103424 A1 | 8/2002 | Swoyer et al. | |
| 2002/0165537 A1 | 11/2002 | Kelley et al. | |
| 2002/0165589 A1 | 11/2002 | Imran et al. | |
| 2002/0183823 A1 | 12/2002 | Pappu | |
| 2002/0183824 A1 | 12/2002 | Borgersen et al. | |
| 2003/0088301 A1 | 5/2003 | King | |
| 2004/0133089 A1 | 7/2004 | Kilcoyne et al. | |
| 2004/0147973 A1 | 7/2004 | Hauser | |
| 2004/0215307 A1 | 10/2004 | Michels et al. | |
| 2004/0230281 A1 | 11/2004 | Heil et al. | |
| 2005/0004602 A1 | 1/2005 | Hart et al. | |
| 2005/0004641 A1 | 1/2005 | Pappu | |
| 2005/0004644 A1 | 1/2005 | Kelsch et al. | |
| 2005/0136385 A1 | 6/2005 | Mann et al. | |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2006/0247753 A1 | 11/2006 | Wenger et al. | |
| 2007/0083230 A1 | 4/2007 | Javois | |
| 2007/0156114 A1 | 7/2007 | Worley et al. | |
| 2007/0219590 A1 | 9/2007 | Hastings et al. | |
| 2008/0057100 A1 | 3/2008 | Williams et al. | |
| 2009/0082828 A1 | 3/2009 | Ostroff | |
| 2010/0094314 A1 | 4/2010 | Hernlund et al. | |
| 2010/0228279 A1 | 9/2010 | Miles et al. | |
| 2010/0274227 A1 | 10/2010 | Khairkhahan et al. | |
| 2011/0144572 A1 | 6/2011 | Kassab et al. | |
| 2011/0251660 A1 | 10/2011 | Griswold | |
| 2012/0059448 A1 | 3/2012 | Parker et al. | |
| 2012/0172690 A1 | 7/2012 | Anderson et al. | |
| 2012/0172892 A1 * | 7/2012 | Grubac | A61N 1/0573 606/129 |
| 2012/0197373 A1 | 8/2012 | Khairkhahan et al. | |
| 2013/0035748 A1 * | 2/2013 | Bonner | A61N 1/056 623/1.11 |
| 2013/0079798 A1 | 3/2013 | Tran et al. | |
| 2013/0103047 A1 | 4/2013 | Steingisser et al. | |
| 2013/0131591 A1 | 5/2013 | Berthiaume et al. | |
| 2013/0131693 A1 | 5/2013 | Berthiaume et al. | |
| 2013/0253347 A1 | 9/2013 | Griswold et al. | |
| 2014/0039591 A1 | 2/2014 | Drasler et al. | |
| 2015/0039070 A1 | 2/2015 | Kuhn et al. | |
| 2015/0051611 A1 | 2/2015 | Schmidt et al. | |
| 2015/0253347 A1 | 9/2015 | Cong et al. | |
| 2015/0352353 A1 | 12/2015 | Rys et al. | |
| 2016/0015322 A1 | 1/2016 | Anderson et al. | |
| 2016/0059003 A1 | 3/2016 | Eggen et al. | |
| 2017/0274202 A1 | 9/2017 | Grubac et al. | |

FOREIGN PATENT DOCUMENTS

| | | |
|---|---|---|
| WO | 2002022202 A2 | 3/2002 |
| WO | 02071977 A2 | 9/2002 |
| WO | 2004028348 A2 | 4/2004 |
| WO | 2005034764 A1 | 4/2005 |
| WO | 2006118865 A2 | 11/2006 |
| WO | 2013043671 | 3/2013 |
| WO | 2013062793 | 5/2013 |
| WO | 2015017157 A1 | 2/2015 |

OTHER PUBLICATIONS

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

(PCT/US2014/057596) PCT Notification of Transmittal of the International Search Report and the Written Opinion of the International Searching Authority, dated Dec. 5, 2014, 12 pages.

(PCT/US2015/040870) PCT Notification of Transmittal of the International Search Report and the Written Opinion of the International Searching Authority, dated Oct. 14, 2015, 10 pages.

(PCT/US2015/043957) PCT Notification of Transmittal of the International Search Report and the Written Opinion of the International Searching Authority, dated Nov. 11, 2015, 9 pages.

(56) References Cited

OTHER PUBLICATIONS (PCT/US2014/057727) PCT Notification of Transmittal of the International Search Report and the Written Opinion of the International Searching Authority, dated Dec. 8, 2014, 12 pages.

Eggen et al., "Interventional Medical Systems, Devices, and Methods of Use" Chinese Patent Application No. 201580045776.8 First Office Action dated Sep. 29, 2018, 7 pages.

Prosecution History from U.S. Appl. No. 14/518,261, dated Mar. 23, 2017 through Jul. 12, 2019, 145 pp.

Response to Written Opinion dated Nov. 11, 2015, from International Application No. PCT/US2014/010345, dated Jun. 27, 2016, 8 pp.

International Preliminary Report on Patentability from International Application No. PCT/US2015/043957, dated Jul. 27, 2016, 5 pp.

Text Intended to Grant from counterpart European Application No. 15753548.5, dated Jul. 24, 2017, 60 pp.

First Office Action and Search Report, and translation thereof, from counterpart Chinese Application No. 201580045776.8, dated Aug. 3, 2018, 8 pp.

\* cited by examiner

INTERVENTIONAL MEDICAL DEVICE AND METHOD OF USE

CROSS-REFERENCE TO RELATED APPLICATION

The present application is a continuation of U.S. patent application having the Ser. No. 14/518,261, which was filed on Oct. 20, 2014, and claims the benefit of U.S. Provisional Patent Application having the Ser. No. 62/041,954, which was filed on Aug. 26, 2014. Application Ser. Nos. 14/518,261 and 62/041,954 are hereby incorporated by reference in their entirety. The present application is related to commonly assigned U.S. patent application Ser. No. 14/518,211, which was filed on Oct. 20, 2014 and entitled INTERVENTIONAL MEDICAL SYSTEMS, DEVICES, AND COMPONENTS THEREOF, and which is incorporated by reference in its entirety.

FIELD OF THE DISCLOSURE

The present disclosure pertains to interventional medical systems, and more particularly to relatively compact implantable medical devices thereof and associated methods.

BACKGROUND

Figure 1:
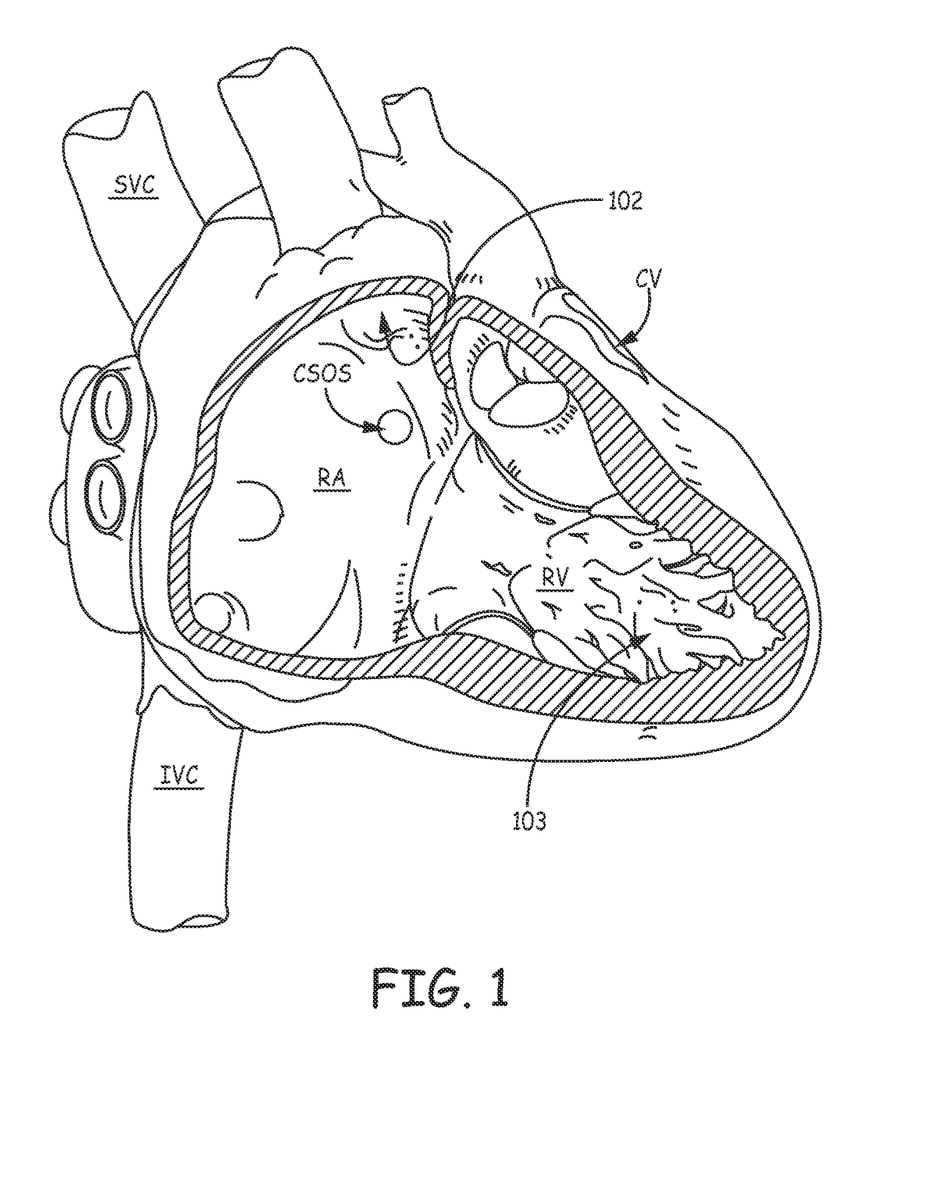
FIG. 1 is a schematic diagram showing potential implant sites for embodiments of the present invention.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MM compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. An implanting physician may employ a standard guiding catheter (not shown) to deliver a relatively compact medical device to any one of the three exemplary sites, for example, according to methods known in the art of interventional cardiology, by maneuvering the catheter, with the device loaded therein, up through the inferior vena cava IVC and into the right atrium RA. However, a co-pending and commonly assigned U.S. patent application having the Ser. No. 14/039,937 discloses a more sophisticated delivery tool, which the operator may employ, in lieu of the standard guiding catheter, to deliver and to fix the device at the desired implant site.

SUMMARY

A relatively compact implantable medical device, according to embodiments of interventional medical systems disclosed herein, includes a fixation member formed by a plurality of fingers mounted around a perimeter of a distal end of a housing of the device; each finger is elastically deformable from a relaxed condition to an extended condition, to accommodate delivery of the device to a target implant site, and from the relaxed condition to a compressed condition, to accommodate wedging of the fingers between opposing tissue surfaces at the target implant site, wherein the compressed fingers hold a cardiac pacing electrode of the device in intimate tissue contact for the delivery of pacing stimulation from the implanted device to the site. According to some methods, after an operator navigates a delivery tool, which has the device loaded within a distal-most portion of a deployment tube thereof, through a venous system of the patient, to locate the distal-most portion of the tool in proximity to a target implant site, the operator retracts the deployment tube with respect to the loaded device to expose the fixation fingers out through a distal opening of the lumen of the deployment tube, so that the fixation fingers are released from the extended condition to the relaxed condition; and then the operator advances the delivery tool toward the target site to wedge the exposed fixation fingers between opposing tissue surfaces at the target implant site, thereby compressing the fixation fingers, so that the compressed fingers, by a spring force thereof, hold the pacing electrode of the device in intimate tissue contact.

Each finger of the device fixation member, according to some embodiments, includes a first segment, which extends from a fixed end of the corresponding finger, and a second segment that extends from the first segment to a free end of the corresponding finger, wherein each second segment extends in a distal direction, when the first segment of each finger is in the extended condition, and extends in a proximal direction, outward from the device housing, when the first segment of each finger is in the relaxed condition. Furthermore, the second segment of each fixation finger is preferably configured to prevent penetration thereof within the tissue when the fingers are compressed and wedged between opposing tissue surfaces.

According to some preferred embodiments, the pacing electrode of the device is mounted on a pacing extension of the device, wherein the pacing extension extends distally from the distal end of the device housing. When the device is loaded in the distal-most portion of the aforementioned delivery tool, an entirety of the pacing extension may be contained within the distal-most portion, along with a remainder of the device and the distal end of the inner member of the tool, which abuts a proximal end of the device housing, and each fixation finger, in the extended condition, extends in a distal direction alongside the pacing extension. According to some embodiments and methods, after navigating the delivery tool to locate the distal-most portion of the tool in proximity to the target implant site, the operator can retract the deployment tube only enough to expose the pacing electrode of the pacing extension without exposing the fixation fingers, and then advance the delivery tool toward the target site until the exposed electrode comes into contact with tissue at the site, so that the operator can evaluate pacing performance at the site. If pacing performance is acceptable at the site, the operator can pull the tool and loaded device back away from the site, retract the deployment tube even further, with respect to the loaded device, to expose the fixation fingers, and then advance the tool again toward the site to wedge the exposed fixation fingers between opposing tissue surfaces at the target implant site, thereby compressing the fixation fingers, so that the compressed fingers hold the pacing electrode in intimate tissue contact.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
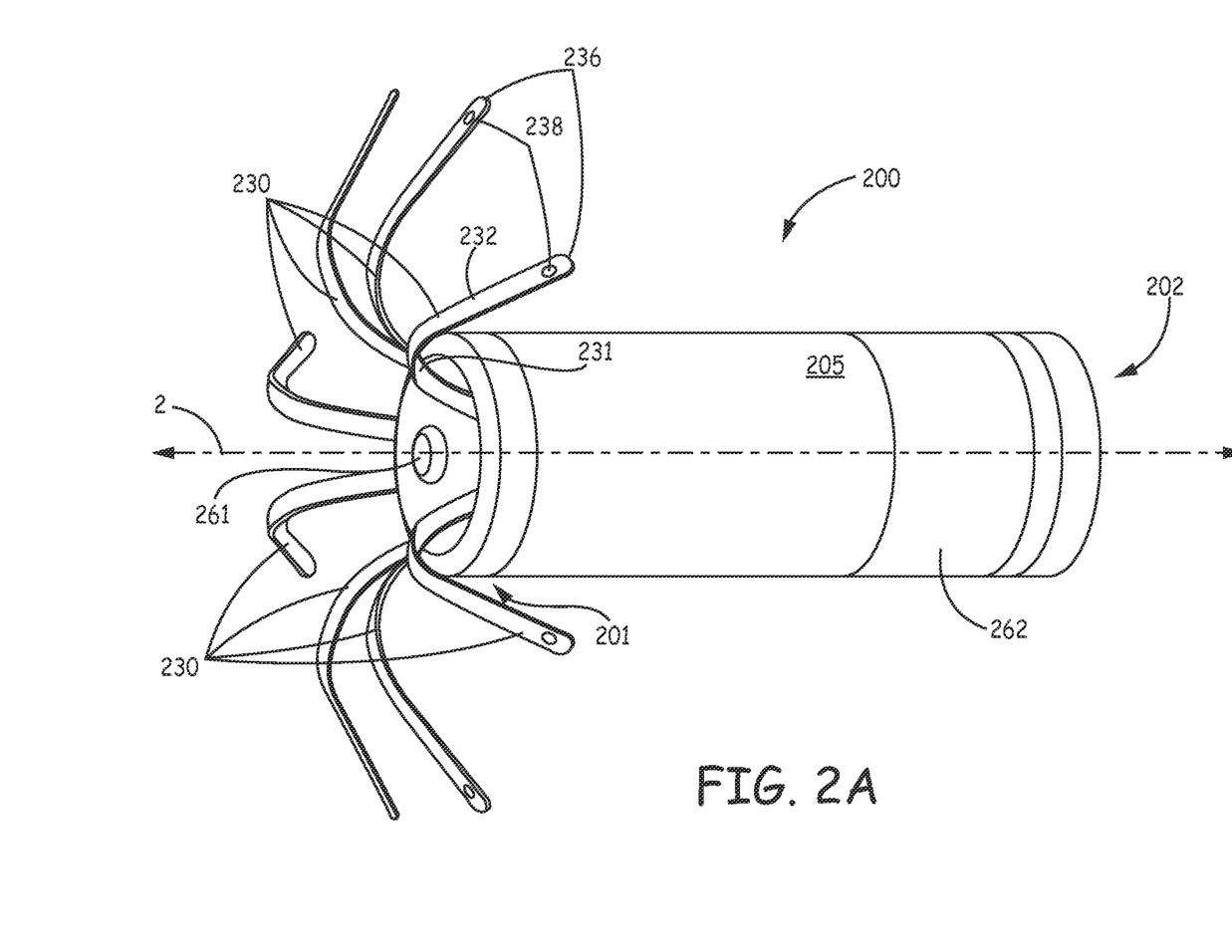
FIG. 2A is a perspective view of an implantable medical device, according to some embodiments.

FIG. 2A is a perspective view of an implantable medical device 200, according to some embodiments. FIG. 2A illustrates device 200 including a hermetically sealed housing 205, preferably formed from a biocompatible and biostable metal such as titanium, which contains a pulse generator (e.g., a power source and an electronic controller—not shown), a fixation member, which is formed by a plurality of fixation fingers 230 spaced apart from one another around a perimeter of a distal end 201 of housing 205, and an electrode 261, which is located at the distal end 201 of housing 205 being coupled to the controller of device 200 by a hermetic feedthrough assembly (not shown) constructed according to those known to those skilled in the art of implantable medical devices. Housing 205 may be overlaid with an insulative layer, for example, medical grade polyurethane, parylene, or silicone, and FIG. 2A further illustrates another electrode 262 of device 200, which may be formed by removing a portion of the insulative layer to expose the metallic surface of housing 205. According to the illustrated embodiment, electrode 262 may function in conjunction with electrode 261 for bipolar pacing and sensing, when fixation fingers 230 hold electrode 261 in intimate tissue contact at a target implant site, for example, within right atrial appendage 102 or within right ventricle RV in proximity to apex 103 (FIG. 1). Fixation fingers 230 function to hold device 200 at the implant site by being wedged between opposing tissue surfaces at the site.

Figure 2B:
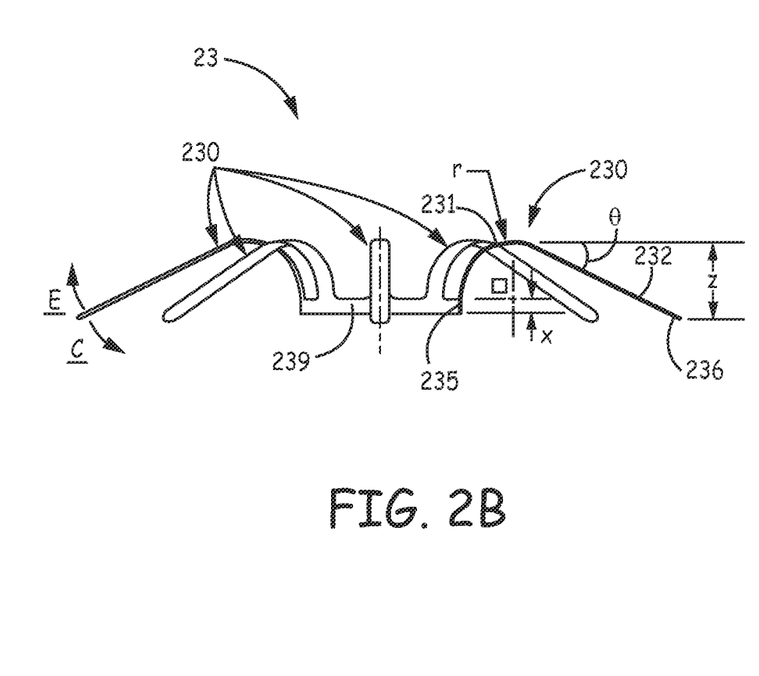
FIGS. 2B-C are elevation and end views of a fixation member component which may be employed by the device of FIG. 2, according to some embodiments.
Figure 2C:
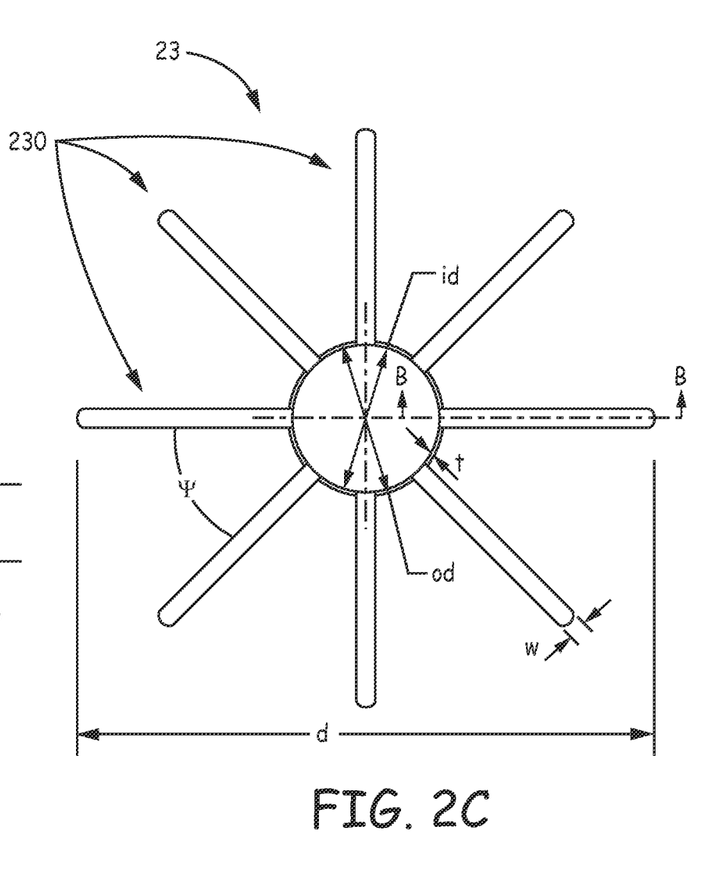

FIGS. 2B-C are elevation and end views of an exemplary fixation member component 23 which may be employed by device 200, according to some embodiments. FIGS. 2B-C illustrate fixation member component 23 including eight fixation fingers 203 integrally formed with one another and a base ring 239, such that a thickness t of base ring 239 is approximately the same as that of each finger 230. According to an exemplary embodiment, fixation member component 23 is cut from Nitinol tubing, according to methods known in the art, and thickness t may be 0.005 inch+/−0.001 inch, wherein base ring 239 may have an inner diameter id of approximately 0.20 inch and an outer diameter od of approximately 0.21 inch. A height x of base ring 239 may be approximately equal to a width w of each finger, for example, approximately 0.024 inch. After cutting the aforementioned Nitinol tubing, fingers 230 are shaped by bending and holding fingers 230 in the illustrated curvature while heat treating component 23 according to methods known to those skilled in the art. FIG. 2B illustrates (via cross-section through section line B-B of FIG. 2C) each fixation finger 230 including a first segment 231 and a second segment 232, wherein each first segment 231 extends from a fixed end 235 of the corresponding finger 230 to the corresponding second segment 232, and each second segment 232 extends from the corresponding first segment 231 to a free end 236 of the corresponding finger 230. FIGS. 2A-B further illustrates each first segment 231, in a relaxed condition, extending in an arc, distally and outwardly from fixed end 235, and second segment 232 extending from first segment 231 in a proximal direction and outward from device housing 205. With further reference to FIG. 2C fixation fingers 230 are spaced equally apart from one another such that an angle ψ defined between each adjacent pair is approximately 45 degrees. Component 23 may be mounted to distal end 201 of device housing 205, for example, in a manner similar to that described for a fixation component 102 in co-pending and commonly assigned United States Patent Application 2012/0172690, which description is hereby incorporated by reference.

Figure 3:
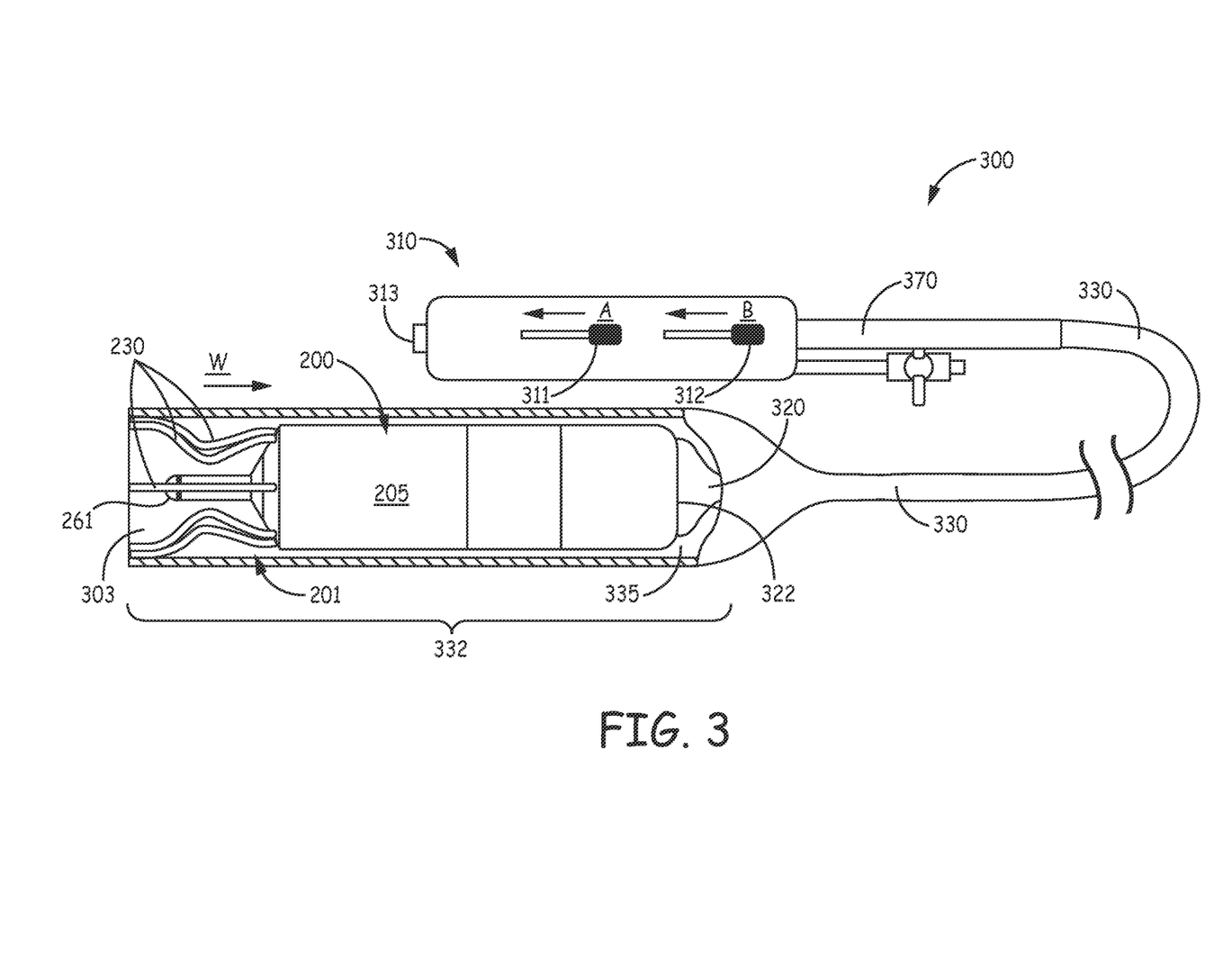
FIG. 3 is a plan view of an interventional medical system with a partial cut-away section, according to some embodiments.
Figures 4A, 4B, 4C:
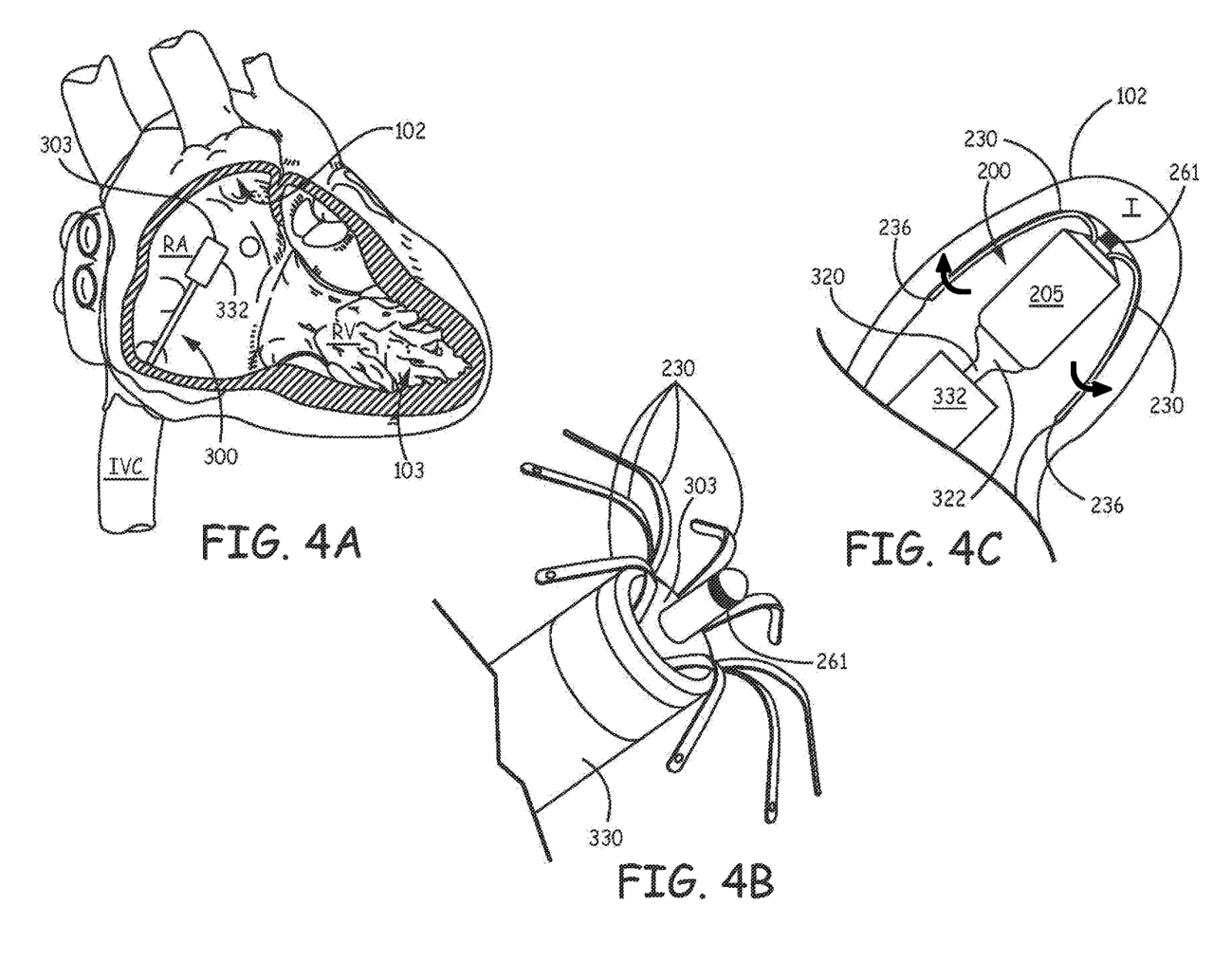
FIGS. 4A-C are schematics outlining some methods of the present invention.

According to the illustrated embodiment, first segment 231 of each fixation finger 230 is elastically deformable between the relaxed condition and an extended condition, per arrow E of FIG. 2B, and between the relaxed condition and a compressed condition, per arrow C of FIG. 2B. The extended condition is described below in conjunction with FIGS. 3, 4A, and 6A-B; and the compressed condition is described below in conjunction with FIGS. 4C and 6C. With further reference to FIG. 2B, the angle enclosed by the arc of first segment 231 of each finger 230 is shown being at least 90 degrees, with second segment 232 extending away from first segment 231 at an angle θ. According to an exemplary embodiment, a radius r of the arc of each first segment 231 is approximately 0.067 inch, and angle θ is approximately 26 degrees. FIG. 2B further illustrates each second segment 232 extending in a proximal direction from first segment 231 over a distance just slightly greater than a distance z, wherein distance z may be approximately 0.095 inch measured from a proximal edge of base ring 239 to a tangent line extending from an intersection of first and second segments 231, 232. Although not shown in FIG. 2A, according to some preferred embodiment, electrode 261 may be mounted on a relatively short extension formed in distal end 201 of housing 205 such that electrode 261 is spaced distal to radius r of each finger 230, for example, as shown in FIGS. 3 and 4B, wherein the distance from the apex of radius r to the distally spaced electrode 261 may be approximately 2 mm. Furthermore, it should be noted that if the exemplary dimensions of component 23, presented in conjunction with FIGS. 2B-C, are scaled down, for example, in proportion to a smaller overall implantable device volume, they will still fall within the scope of embodiments of the present invention.

FIG. 3 is a plan view of an interventional medical system with a partial cut-away section, according to some embodiments, wherein the system includes a delivery tool 300, in which device 200 is loaded, for deploying device 200 to a target implant site. FIG. 3 illustrates tool 300 including a handle 310, an elongate inner member 320, and an outer assembly, which is formed by an elongate deployment tube 330 and an outer, stabilizing sheath 370 that is secured to handle 310 and surrounds a proximal portion of deployment tube 330 in proximity to handle 310. According to the illustrated embodiment, elongate inner member 320 extends within a lumen 335 of deployment tube 330, and a proximal end of deployment tube 330 is coupled to a control member 312 of handle 310 such that an entirety of deployment tube 330 is movable with respect to the inner member 320, via control member 312. FIG. 3 further illustrates inner member 320 including a distal end 322, which is located within a distal-most portion 332 of deployment tube 330, and which is configured to engage implantable medical device 200 by abutting proximal end 202 of device housing 205, as shown.

With further reference to FIG. 3, that portion of deployment tube lumen 335 which extends along a length of distal-most portion 332 is sized to contain distal end 322 of inner member 320 together with an entirety of device 200. FIG. 3 shows fixation fingers 230 of the loaded device 200 being held by distal-most portion 332 in the aforementioned extended position. With reference to FIG. 4A, a distal portion of tool 300, with an entirety of device 200 loaded in distal-most portion 332, may be navigated to a target implant site, for example, in the right atrium RA (or right ventricle RV), by advancing tool 300 through a venous system of the patient, for example, from a femoral venous access site and up through the inferior vena cava IVC. A length of deployment tube 330, between handle 310 and a distal opening 303 of deployment tube 330, when tube 330 is in the position shown in FIG. 3, may be between approximately 103 cm and approximately 107 cm, for example, to reach the right atrium RA from the femoral access site. According to some embodiments of the present invention, delivery tool 300 includes articulating features to facilitate the navigation of the distal portion of delivery tool 300; for example, inner member 320 of delivery tool 300 may include a pull wire (not shown) integrated therein and coupled to another control member 311 of handle 310 that, when moved per arrow A, causes inner member 320 and deployment tube 330 to bend along distal portions thereof. Suitable construction detail for a delivery tool like tool 300 is described in co-pending and commonly assigned U.S. patent application Ser. No. 14/039,937, the description of which is hereby incorporated by reference.

According to some methods of the present invention, once an operator has located distal-most portion 332 in a chamber of the heart, for example, the right atrium RA, as shown in FIG. 4A, the operator can retract deployment tube 330, per arrow W (FIG. 3), for example, by moving control member 312 per arrow B (FIG. 3), to release fixation fingers 230 to the relaxed position as shown in FIG. 4B. FIG. 4B illustrates each finger 230 having been exposed out through distal opening 303 of deployment tube 330 so that, in the relaxed position, each finger 230 extends in a proximal direction and outward from device housing 205. Then, after releasing device fixation fingers 230, the operator may advance tool 300 and device 200 together to a target implant site between folds of tissue, for example, pectinate muscle bands in right atrial appendage 102, and, thus, wedge the exposed fixation fingers 230 between opposing tissue surfaces as shown schematically in FIG. 4C. With reference to FIG. 4C, distal end 322 of device inner member 320 may be employed to provide a push force that assists in wedging fingers 230 so that fingers 230 are in the aforementioned compressed state to hold electrode 261 in intimate tissue contact. With reference back to FIG. 2, according to some embodiments, one or more of finger free ends 236 includes a discrete radiopaque marker 238 attached thereto, for example, a platinum-iridium rivet like member. Optional marker(s) 238 may assist the operator in assessing the fixation of device 200 at the implant site. It should be noted that the compressed fingers 230, having a super-elastic nature, hold device 200 in place at the implant site by a spring force (per the bold arrows of FIG. 4C), and that finger free ends 236 are preferably configured to prevent penetration thereof within tissue at the implant site, while merely catching, or lodging against opposing tissue surfaces. Furthermore, with reference to FIG. 4A, an alternate implant site may be in the right ventricle RV, where fixation fingers 230 may be wedged between folds of tissue (trabeculae) in the area of apex 103. It should be noted that the fixation fingers 230, as described above in conjunction with FIGS. 2B-C, may also be formed from a polymer material, either individually or integrally with base ring 239, wherein an appropriate polymer material and associated dimensional specifications essentially mimics that of fingers 230 formed from the aforementioned Nitinol, in terms of spring properties.

After wedging fingers 230 between opposing tissue surface, the operator may evaluate pacing performance of electrode 261 before completely withdrawing delivery tool 300 away from the implanted device 200. Thus, if the operator determines that the performance is not satisfactory, the operator may advance distal-most portion 332 of deployment tube 330 back in a distal direction, for example, via control member 312 (FIG. 3), relative to device 200 and inner member 320 and over wedged fixation fingers 230 to move device 200 back into distal-most portion 332 with fingers 230 moved back into the extended condition, as shown in FIG. 3. Then the operator can move delivery tool 300 with the re-loaded device 200 into proximity with an alternative implant site, retract deployment tube 330 again to expose and release fingers 230 into the relaxed condition (FIG. 4B), and then advance tool 300 toward the other site to wedge the exposed fingers 230 between opposing tissue surfaces at the other site (FIG. 4C).

Figure 5A:
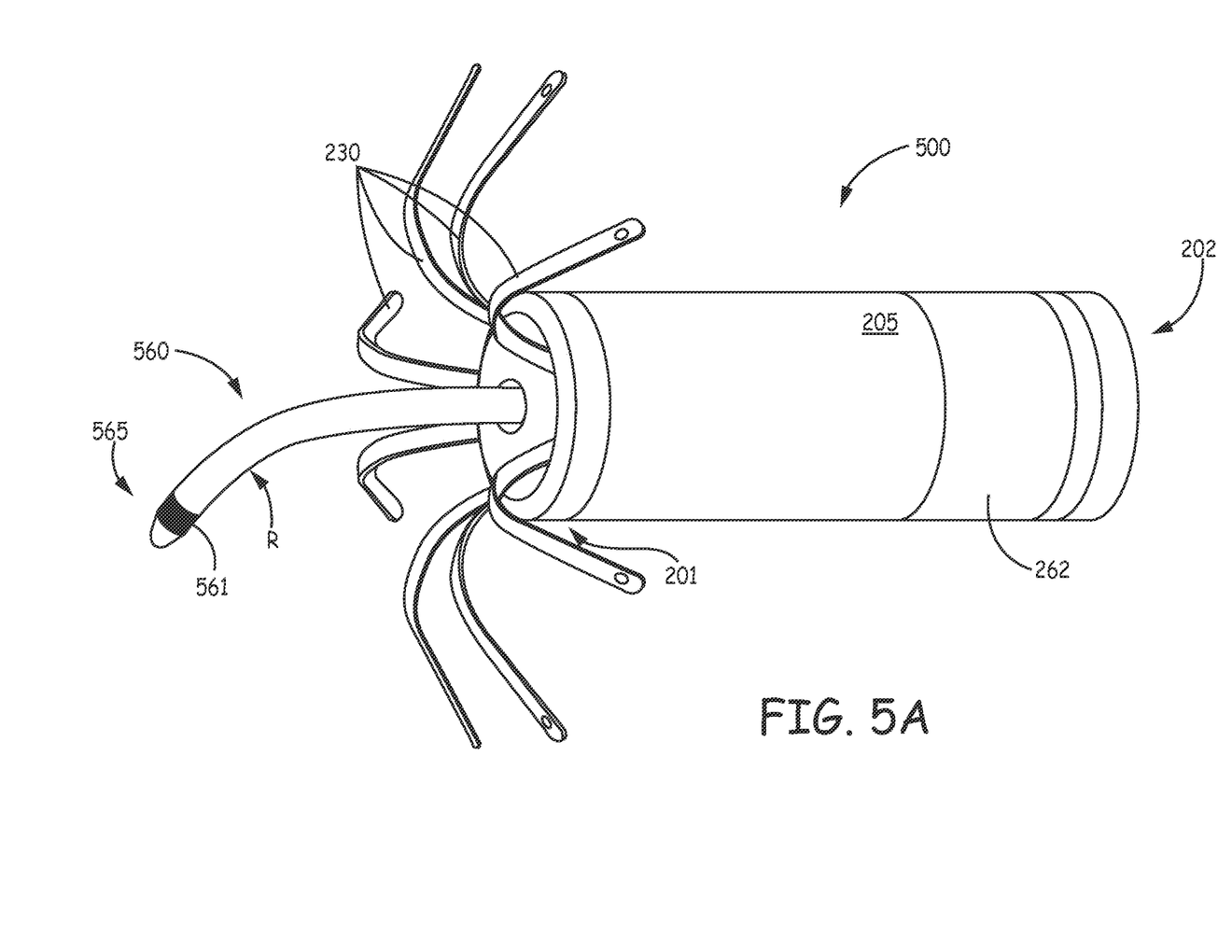
FIG. 5A is a perspective view of an implantable medical device, according to some additional embodiments.
Figure 5B:
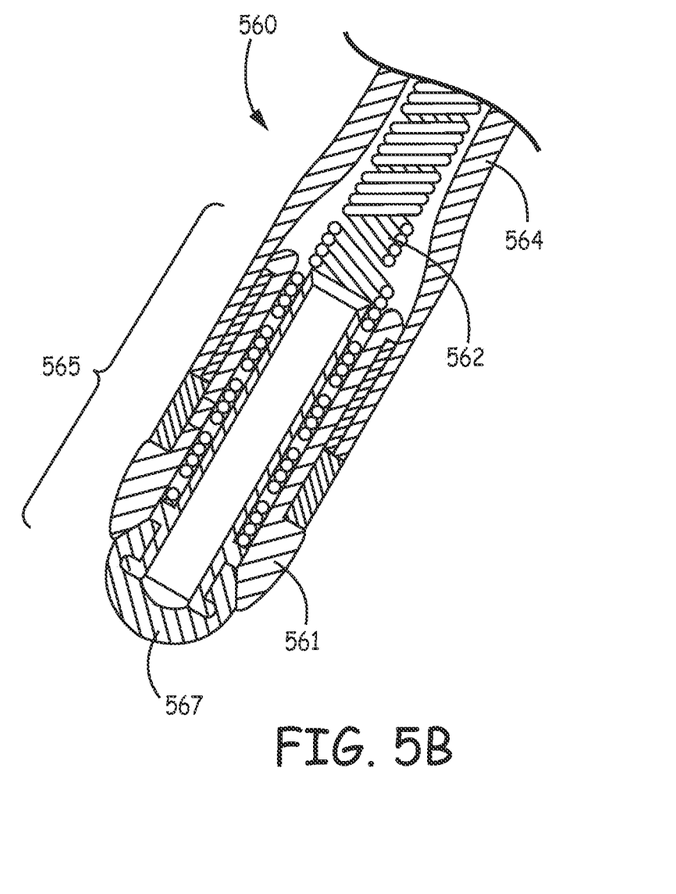
FIG. 5B is a cross-section view through a portion of the device of FIG. 5A, according to an exemplary construction of some embodiments.

FIG. 5A is a perspective view of an implantable medical device 500, according to some additional embodiments; and FIG. 5B is a cross-section view through a portion of device 500, according to an exemplary construction of some embodiments. FIG. 5A illustrates device 500 being similar to device 200 but including a pacing extension 560 on which a pacing electrode 561 is mounted, in lieu of electrode 261 of device 200. FIG. 5A further illustrates extension 560 including a preformed curvature located in proximity to, and proximal to electrode 561. A diameter of extension 560 may be approximately 0.05 inch (1.3 mm); an overall length of extension 560 may be approximately 0.6 inch (15 mm); and the curvature, preferably in a single plane, is defined by a radius R, which may be approximately 0.2 inch, according to an exemplary embodiment. According to the illustrated embodiment, electrode 561 is located in close proximity to a distal tip 565 of extension 560, which tip 565 is preferably tapered. FIG. 5B illustrates distal tip 565 being slightly enlarged from a remainder of extension 560; and, according to some embodiments, tip 565 includes electrode 561, which forms at least a portion of the taper, and a relatively soft medical grade silicone rubber member 567, which may include a steroid embedded therein. The illustrated contour of electrode 561 may help electrode 561 to make better tissue contact when tip 565 lies adjacent to tissue, for example, as illustrated in FIG. 6C. According to an exemplary embodiment, a diameter of tip 565 (as shown in FIG. 5B) is approximately 0.07 inch (1.8 mm), and a surface area of electrode 561 is approximately 5.8 mm$^2$. Electrode 561 may be formed from a platinum iridium alloy.

FIG. 5B further illustrates pacing extension 560 being formed by a coiled multi-filar conductor 562 (e.g., MP35N alloy) enclosed within a jacket of insulation 564 (e.g., medical grade polyurethane), and an exemplary junction between electrode 561 and conductor 562, which may be secured by crimping and/or welding according to methods known in the art of implantable medical electrical leads. According to the illustrated embodiment, conductor 562 electrically connects electrode 561 to the aforementioned pulse generator contained within device housing 205, for example, via a feedthrough assembly constructed according to methods known in the art of implantable medical devices.

Figure 6A:
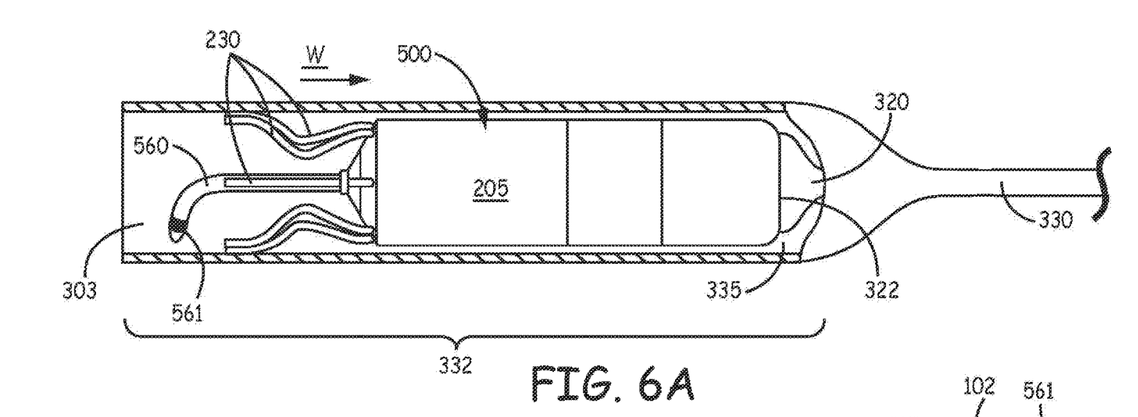
FIGS. 6A-C are schematics according to some alternate methods of the present invention.
Figure 6B:
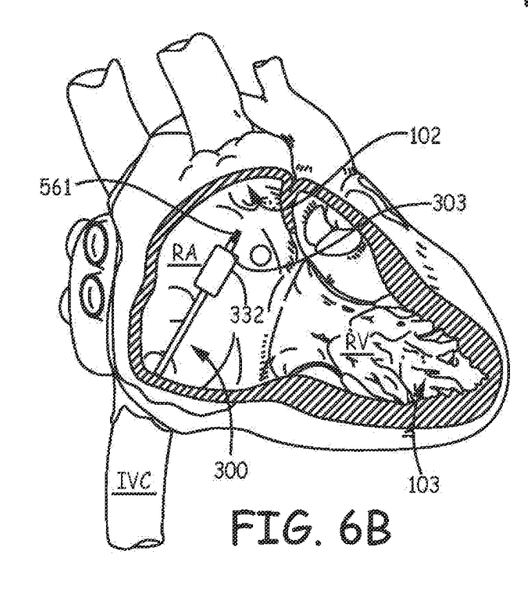
Figure 6C:
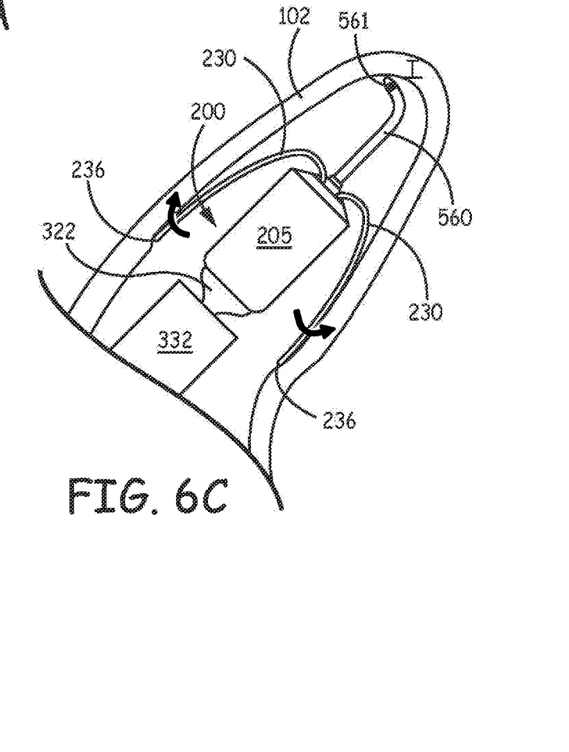

Turning now to FIG. 6A, as was described above for device 200, device 500 is loaded into distal-most portion 332 of delivery tool 300 (FIG. 3), such that fixation fingers 230 are in the extended condition. FIG. 6A illustrates fingers 230 extending in a distal direction and alongside pacing extension 560 within distal-most portion 332. After device 500 is loaded, the operator may navigate delivery tool 300, with device 500 completely contained therein, through the patient's venous system, for example, from a femoral venous access site, up through the inferior vena cava IVC, and into a chamber of the heart, for example, the right atrium RA, as shown in FIG. 4A. In some preferred embodiments, pacing extension 560 extends distally beyond extended fingers 230 so that the operator may withdraw deployment tube 330, per arrow W, just enough to expose electrode 561 out through distal opening 303 thereof, as shown in FIG. 6B. According to some exemplary embodiments, extension 560 can extend approximately 2 to 4 mm beyond opening 303 without fingers 230 being exposed, so that the operator can advance tool 300 to one or more potential implant sites, where electrode 561 makes contact, to map electrical activity and/or to check pacing thresholds. According to some methods, after finding a desired implant site in this manner, the operator can pull back tool 300 and device 500 together, for example, to the position shown in FIG. 6B, and then retract deployment tube 330 even further, with respect to device 500 and inner member 320, to expose fixation fingers 230 out from distal opening 303, thereby releasing fingers 230 to the relaxed condition (FIG. 4B). Then, as described above, the operator can advance tool 300 and device 500 together back to the desired implant site, for example, between pectinate muscle bands in right atrial appendage 102, and, thus, wedge the exposed fixation fingers 230 between opposing tissue surfaces as shown schematically in FIG. 6C, to hold device 500 at the implant site with electrode 561 making intimate tissue contact. With further reference to FIG. 6C, it may be appreciated that the length of pacing extension 560 serves to separate that portion of the implant site at which electrode 561 makes contact with that portion of the site at which fixation fingers 230 make spring contact (e.g., per bold arrows), so that any inflammation associated with the fixation fingers contact may not impair chronic pacing thresholds.

Figure 7:
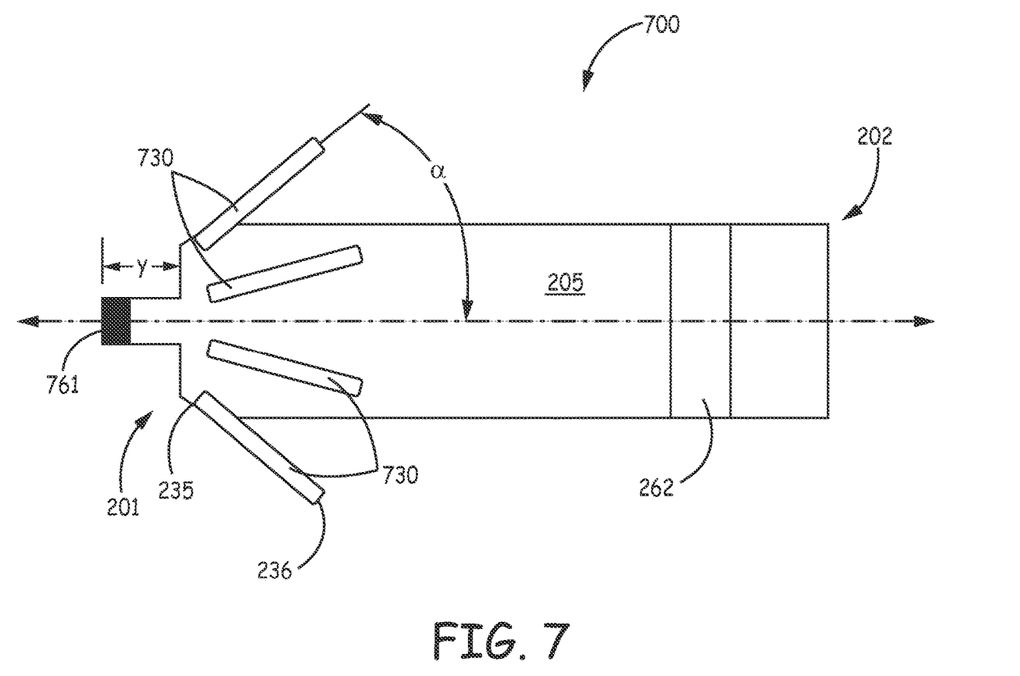
FIG. 7 is a perspective view of an implantable medical device, according to some alternate embodiments.

FIG. 7 is a plan view of an implantable medical device 700, according to some alternate embodiments. FIG. 7 illustrates device 700 being similar to device 200 of FIG. 2, in that device 700 includes hermetically sealed housing 205, which may be overlaid with an insulative layer, for example, medical grade polyurethane, parylene, or silicone, and wherein electrode 262 may be formed by removing a portion of the insulative layer to expose the metallic surface of housing 205. FIG. 7 further illustrates device 700 including a fixation member, which is formed by a plurality of fixation fingers 730, for example, eight fingers, spaced apart from one another around a perimeter of a distal end 201 of housing 205, and an electrode 761, which is spaced distally apart from distal end 201 of housing 205 by a distance y, which may be approximately 2 mm, for example, to allow electrode 761 to make better tissue contact along uneven surfaces such as between pockets created by relatively small pectinate muscle bands in right atrial appendage 102 (FIG. 1). With reference back to FIG. 2A, it should be noted that electrode 261 of device 200 may be similarly spaced from distal end 201 of housing 205. Electrode 761, like electrode 261, may be coupled to the controller of device 200 by a hermetic feedthrough assembly to function in conjunction with electrode 262 for bipolar pacing and sensing.

According to the illustrated embodiment, fixation fingers 730 are formed from a flexible polymer material, for example, medical grade silicone rubber or polyurethane, and, in a relaxed condition, extend proximally from distal end 201 of device housing 205, and outward therefrom at an angle α relative to a longitudinal axis of device housing 205. Angle α may be approximately 60 degrees, and a length of each finger 730, from a fixed end 735 to a free end 736 thereof, may be approximately 0.2 inch (5 mm). Like the above described fixation fingers 230, fingers 730 are configured to hold electrode 761 in intimate tissue contact at a target implant site, for example, within right atrial appendage 102 or within right ventricle RV in proximity to apex 103 (FIG. 1), but, being relatively softer than Nitinol, silicone rubber or polyurethane fingers may be less likely to migrate through tissue at the implant site over time.

In the foregoing detailed description, the invention has been described with reference to specific embodiments. However, it may be appreciated that various modifications and changes can be made without departing from the scope of the invention as set forth in the appended claims.

We claim:
1. An implantable medical device comprising:
a device housing;
a pacing extension extending distally from a distal end of the device housing;
a pacing electrode mounted on a distal end of the pacing extension; and
a fixation member attached to the distal end of the device housing, the fixation member comprising a plurality of fingers,
wherein each finger extends from a fixed end to an arc and from the arc to a free end, wherein the arc defines an apex distal to the distal end of the housing, and wherein the each finger is configured to assume a relaxed condition and an extended condition, wherein:
the free end is proximal to the fixed end, proximal to the arc, and outward of the apex of the arc in the relaxed condition, such that the arc is between the free end and a longitudinal axis of the device housing when the each finger is in the relaxed condition,
the free end is distal to the fixed end, distal to the arc, and distal to the distal end of the device housing in the extended condition, the pacing electrode is distal to the arc in the relaxed condition, the each finger is configured to generate a spring force acting in a direction away from the device housing when the free end is displaced toward the device housing, the plurality of fingers are configured to hold the pacing electrode against tissue when the free end of the each finger is displaced from the relaxed condition and toward the housing by a tissue surface, and the plurality of fingers surround the longitudinal axis such that a first finger of the plurality of fingers contacts a first tissue surface and a second finger of the plurality of fingers contacts a second tissue surface opposing the first tissue surface when the plurality of fingers hold the pacing electrode against tissue.

2. The implantable medical device of claim 1, wherein the pacing electrode is distal to the free end in the extended condition.

3. The implantable medical device of claim 1, wherein the arc encloses an angle of at least ninety degrees in the relaxed condition.

4. The implantable medical device of claim 1 wherein the free end is a rounded end configured to prevent tissue penetration.

5. The implantable medical device of claim 1 wherein each finger is elastically deformable between the relaxed condition and the extended condition, and each finger is configured to transition from the extended condition to the relaxed condition and configured to transition from the relaxed condition to the extended condition.

6. The system of claim 1, wherein the plurality of device fingers comprises up to eight fingers spaced equally apart from one another around a perimeter of the device housing.

7. The implantable medical device of claim 1 further comprising an electronic controller within the device housing and coupled to the electrode.

8. The implantable medical device of claim 1, wherein the pacing extension of the device includes a tapered distal tip, and the electrode of the device forms at least a portion of the tapered distal tip.

9. The implantable medical device of claim 1, wherein each finger further includes a discrete radiopaque marker located in proximity to the free end thereof.

10. An implantable medical device comprising:
a device housing;
a pacing extension extending distally from a distal end of the device housing;
a pacing electrode mounted on a distal end of the pacing extension; and
a fixation member attached to the distal end of the device housing, the fixation member comprising a plurality of fingers,
wherein each finger extends from a fixed end to an arc and from the arc to a free end, wherein the arc defines an apex distal to the distal end of the housing, wherein each finger is configured to assume a relaxed condition and an extended condition, wherein each finger generates a spring force acting in a direction to return the finger to the relaxed condition when some portion of the finger is displaced toward the device housing from the relaxed condition, and wherein:
the free end is proximal to the fixed end, proximal to the arc, and outward of the apex of the arc in the relaxed condition, such that the arc is between the free end and a longitudinal axis of the device housing when the each finger is in the relaxed condition,
the free end is distal to the fixed end, distal to the arc, and distal to the distal end of the device housing in the extended condition,
the pacing electrode is distal to the arc in the relaxed condition and distal to the free end in the extended condition,
the each finger is configured to generate a spring force acting in a direction away from the device housing when the free end is displaced toward the device housing,
the plurality of fingers are configured to hold the pacing electrode against tissue when the free end of the each finger is displaced from the relaxed condition and toward the housing by a tissue surface, and
the plurality of fingers surround the longitudinal axis such that a first finger of the plurality of fingers contacts a first tissue surface and a second finger of the plurality of fingers contacts a second tissue surface opposing the first tissue surface when the plurality of fingers hold the pacing electrode against tissue.

11. The implantable medical device of claim 10, further comprising a deployment tube having a lumen and the lumen surrounding the plurality of fingers, wherein the deployment tube is configured to be slidably translatable over the plurality of fingers when each finger in the plurality of fingers is in the extended condition.

12. The implantable medical device of claim 11, wherein each finger is configured to transition from the extended condition to the relaxed condition when each finger is in the extended condition and the deployment tube slidably translates over the plurality of fingers in a direction from the distal end of the device housing toward a proximal end of the device housing.

13. The implantable medical device of claim 12, wherein each finger is configured to transition from the relaxed condition to the extended condition when each finger is in the relaxed condition and the deployment tube slidably translates over the plurality of fingers in a direction from the proximal end of the device housing toward the distal end of the device housing.

14. The implantable medical device of claim 13 further comprising an elongate inner member configured to extend through the lumen and abut the proximal end of the device housing, wherein the elongate inner member is configured to be movable with respect to the deployment tube when the elongate inner member extends through the lumen.

15. A medical system comprising:
an implantable medical device comprising:
a device housing;
a pacing extension extending distally from a distal end of the device housing;
a pacing electrode mounted on a distal end of the pacing extension;
a fixation member attached to the distal end of the device housing, the fixation member comprising a plurality of fingers,
wherein each finger extends from a fixed end to an arc and from the arc to a free end, wherein the arc defines an apex distal to the distal end of the housing, and wherein each finger is configured to assume a relaxed condition and an extended condition, wherein:
the free end is proximal to the fixed end, proximal to the arc, and outward of the apex of the arc in the relaxed condition, such that the arc is between the free end and a longitudinal axis of the device housing when the each finger is in the relaxed condition, the free end is distal to the fixed end, distal to the arc, and distal to the distal end of the device housing in the extended condition, the pacing electrode is distal to the arc in the relaxed condition, the each finger is configured to generate a spring force acting in a direction away from the device housing when the free end is displaced toward the device housing, the plurality of fingers are configured to hold the pacing electrode against tissue when the free end of the each finger is displaced from the relaxed condition and toward the housing by a tissue surface, and the plurality of fingers surround the longitudinal axis such that a first finger of the plurality of fingers contacts a first tissue surface and a second finger of the plurality of fingers contacts a second tissue surface opposing the first tissue surface when the plurality of fingers hold the pacing electrode against tissue; and a deployment tube having a lumen and the lumen surrounding the plurality of fingers, wherein the deployment tube is configured to be slidably translatable over the plurality of fingers when each finger in the plurality of fingers is in the extended condition.

16. The medical system of claim 15, wherein each finger is configured to transition from the extended condition to the relaxed condition when each finger is in the extended condition and the deployment tube slidably translates over the plurality of fingers in a direction from the distal end of the device housing toward a proximal end of the device housing.

17. The medical system of claim 16, wherein each finger is configured to transition from the relaxed condition to the extended condition when each finger is in the relaxed condition and the deployment tube slidably translates over the plurality of fingers in a direction from the proximal end of the device housing toward the distal end of the device housing.

18. The medical system of claim 15 further comprising an elongate inner member configured to extend through the lumen and abut a proximal end of the device housing, wherein the elongate inner member is configured to be movable with respect to the deployment tube when the elongate inner member extends through the lumen.

19. The medical system of claim 18 further comprising a handle secured to a proximal end of the elongate inner member, wherein the handle comprises a control member coupled to a proximal end of the deployment tube.

20. The medical system of claim 1, wherein the plurality of fingers are configured to hold the pacing electrode against tissue when the each finger is compressed toward the housing by the tissue surface, such that the each finger is between the tissue surface and the housing.

* * * * *